United States Patent
Holte et al.

(10) Patent No.: US 11,820,685 B2
(45) Date of Patent: Nov. 21, 2023

(54) TWO-TIMES-TWO TANK PROCESS AND SYSTEM

(71) Applicant: Cambi Technology AS, Asker (NO)

(72) Inventors: Hans Rasmus Holte, Reistad (NO); Andreas Helland Lillebo, Oslo (NO)

(73) Assignee: Cambi Technology AS, Asker (NO)

( * ) Notice: Subject to any disclaimer, the term of this patent is extended or adjusted under 35 U.S.C. 154(b) by 237 days.

(21) Appl. No.: 17/309,672

(22) PCT Filed: Nov. 28, 2019

(86) PCT No.: PCT/EP2019/082945
§ 371 (c)(1),
(2) Date: Jun. 14, 2021

(87) PCT Pub. No.: WO2020/126397
PCT Pub. Date: Jun. 25, 2020

(65) Prior Publication Data
US 2022/0017397 A1    Jan. 20, 2022

(30) Foreign Application Priority Data
Dec. 17, 2018   (EP) .................................... 18213186

(51) Int. Cl.
C02F 11/04   (2006.01)
C02F 3/28    (2023.01)
C02F 11/18   (2006.01)

(52) U.S. Cl.
CPC ............ C02F 11/04 (2013.01); C02F 3/2866 (2013.01); C02F 11/18 (2013.01)

(58) Field of Classification Search
CPC ........ C02F 11/04; C02F 3/2866; C02F 11/18; C12P 2201/00; C12P 5/023; Y02E 50/30; Y02P 20/582

USPC ......................... 210/603, 612, 613, 252, 259
See application file for complete search history.

(56) References Cited

U.S. PATENT DOCUMENTS

| 10,358,357 B2* | 7/2019 | DiMassimo | ............ C02F 11/13 |
| 2007/0098625 A1* | 5/2007 | Adams | ..................... C10G 1/10 |
| | | | 423/484 |

FOREIGN PATENT DOCUMENTS

| EP | 3156374 A2 | 4/2017 |
| KR | 20040028696 A * | 4/2004 |
| WO | WO 2010/151706 A1 * | 12/2010 |
| WO | 2011006854 A1 | 1/2011 |
| WO | WO 2014/026154 A1 * | 2/2014 |
| WO | 2017023561 A1 | 2/2017 |

OTHER PUBLICATIONS

Machine-generated English translation of KR 20040028696, generated on Apr. 19, 2023.*

* cited by examiner

*Primary Examiner* — Fred Prince
(74) *Attorney, Agent, or Firm* — Downs Rachlin Martin PLLC (57) ABSTRACT

A method and plant for hydrolysis of a liquid substrate, having a dry solids content of between 2 and 30%, to be used in an anaerobic fermentation, digestion or another process aimed at producing or extracting methane or other valuable substances, which method and plant relies on the use of vacuum and several pulpers and one or several flashtanks in series for step-wise pre-heating and pressure reduction, respectively.

19 Claims, 4 Drawing Sheets

TWO-TIMES-TWO TANK PROCESS AND SYSTEM

FIELD OF THE INVENTION

The present invention relates to methods and plants employing Thermal Hydrolysis Processes (THP), which make use of pulpers and flashtanks for pre-heating and, pressure reduction, respectively. The present invention also relates to methods for retrofitting existing plants employing Thermal Hydrolysis Processes (THP).

BACKGROUND OF THE INVENTION

A Thermal Hydrolysis Process (THP) is a process where a wet or moist material is treated at elevated temperatures, typically between 140 to 220 C, which may be followed by a steam explosion by a rapid reduction in the partial pressure of steam.

THP followed by steam explosion is mostly used for pre-treatment of biosolids prior to anaerobic digestion. However, other materials can be pre-treated in the same manner, following which they can be further processed via a wide range of other down-stream processes.

Thermal Hydrolysis Processes (THP) may be designed for either batch or continuous mode. The methods and plants of the present invention is relevant for both THP designed for batch and THP designed for continuous mode. Furthermore, the methods of the present invention can be used in both new plants or implemented into existing plants by retrofitting, involving installing relevant additional equipment and making relevant modifications.

Material that is treated in a THP can be referred to as "substrate". The substrate is treated with a desired partial pressure of steam. In a batch process, the time the substrate is kept at the desired conditions in the reactor is referred to as "retention time". For a continuous process, the average reactor residence time is a value, which can be calculated from the overall through-put of the overall process.

The substrate will experience a rapid pressure reduction and undergo steam-explosion as it is discharged from the THP reactor, through a nozzle, to a flashtank. This opens cell walls, disintegrates organic materials, reduces particle sizes and viscosity of the substrate. The flash-steam resulting from the steam-explosion can be used to pre-heat substrate in a pressure vessel that can be referred to as a pulper. The use of flash-steam to pre-heat substrate prior to reactor treatment is important for achieving a high energy efficiency and a low steam consumption.

WO/1996/009882 (U.S. Pat. No. 5,888,307) describes methods and means for hydrolysis of organic materials. The processes described neither involves the use of vacuum, flashing below ambient pressure nor the use of the resulting flash steam from any such process for direct steam injection to pre-heat incoming feed.

WO/2011/006854 describes methods and means for hydrolysis of organic materials involving THP and steam explosion, in which steam resulting from flashing is returned to the preheating tank. The process described in WO/2011/006854 uses either liquid or steam at high pressure to generate a motive flow in an ejector to mix steam entering the suction side into the main flow discharged to a vessel at ambient or higher pressure.

The process described in the present invention is different since the system used to generate a vacuum does not work on steam, but instead only on non-condensable gases. This allows the system used to generate a vacuum in the present invention to operate at lower pressures, temperatures, volume flow rates and mass flow rates compared to the process described in WO/2011/006854. This makes the system described in the present invention more energy efficient, more robust and easier to operate compared to the process described in WO/2011/006854.

WO/2014/123426 describes further methods and means for hydrolysis of organic materials involving THP and steam explosion. Similar to WO/1996/009882 (U.S. Pat. No. 5,888,307), this process neither involves the use of vacuum, flashing below ambient pressure nor the use of the resulting flash steam from any such process for direct steam injection to pre-heat incoming feed.

US2003121851 describes methods and means for hydrolysis of organic material involving the addition of KOH and a dewatering step following THP. The flash steam recovery is similar to what is described in WO/1996/009882 and, consequently, neither involves the use of vacuum, flashing below ambient pressure nor the use of the resulting flash steam from any such process for direct steam injection to pre-heat incoming feed. U.S. Pat. No. 6,281,300 describes methods and means for hydrolysis of organic material. The processes described does not involve the use of vacuum. Furthermore, the process is specifically designed for production of polymers which, is not the purpose of present innovation. Polymers may be a proportion of the substrates treated in present innovation, and furthermore some polymerization may take place. However, the main purpose of the present innovation is to hydrolyse and steam explode prior to downstream processing. Examples of downstream treatment includes, but is not limited to, dewatering, enzyme treatment, anaerobic digestion and fermentation.

US2014120594 describes methods and means for hydrolysis of organic material, and is focused on the pre-treatment of woody feedstocks for production of sugars that are fermented into "alcohols". It is described that the processes can have up to 8 flashing stages and that flash steam can be used for pre-heating. Even if vacuum and pressures below ambient are mentioned this is in connection with evaporators in an attempt to concentrate the treated material, and, thus, not for direct steam injection for pre-heating of feed.

US2018201517 describes methods and means for hydrolysis of organic material, and mentions that the hydrolyzed substrate can be passed through a waste heat boiler to produce steam. The use of vacuum is not mentioned, and the processes described would require large heating surfaces due to poor heat transfer, scaling and fouling issues with viscous hydrolyzed substrates. Furthermore, the processes described would not enable the production of steam at lower than ambient pressure. In comparison, the present invention overcomes (or rather by-passes) the heat transfer issue and risk of scaling and fouling by making use of direct steam injection and also allows steam at lower than ambient pressure to be used to pre-heat substrate.

US2009032464 describes methods and means for hydrolysis of organic material, and mentions that flashing can take place under vacuum conditions. However, in the processes described the flash steam goes to a heat exchanger, which could possibly function as a condenser cooler. It also describes closed loops with a circulated cooling/heating media for recovery of heat for preheating substrate and for drying purposes. In contrast the present invention contemplates making use of the flash steam for pre-heating of the feed by direct steam injection.

CA2992657 describes a process for thermal hydrolysis of substrate making use of least three THP reactors in parallel. The use of vacuum is not mentioned, and the processes described does not involve the use of the resulting flash steam from any such process for direct steam injection to pre-heat incoming feed in pulper WO2013163998 (A1) describes a method for continuous treatment of biological material at an elevated pressure before anaerobic digestion in which the biological material is transferred from the infeed device to a reactor by means of pressure differences or gravity. The use of vacuum is not mentioned, and the processes described does not involve the use of the resulting flash steam from any such process for direct steam injection to pre-heat incoming feed in pulper.

As can be seen from the above relevant methods and plants known from the prior art mostly are described as having one preheating step and one flashing step, and the substrate fed to the process is about 10-30 C, and most commonly about 15 C. Also, even if multiple flashtanks and vacuum and pressures below ambient are mentioned in the prior art, this is in connection with condenser coolers or evaporators used in an attempt to concentrate the treated material, and, thus, not for direct steam injection for pre-heating of feed in a pre-heating vessel maintained below ambient pressure. Thus, the prior art does not encompass a method involving flashing below ambient pressure and using the resulting flash steam for direct steam injection to pre-heat incoming feed in a pre-heating vessel maintained below ambient pressure to facilitate the flash steam transfer.

In contrast to the prior art the present invention relies on maintaining parts of the system below ambient pressure by removing non-condensable gases by using a vacuum system and at least two pulpers and two flashtanks in series for step-wise pre-heating and pressure reduction, respectively, by injection of flashsteam below liquid level in both pulpers. Alternatively, the system can be fitted with one less flashtank than the number of pipers, but minimum two pulpers and one flashtank, if the reactors are allowed to depressurize by transferring flash steam from the reactor headspace to the pulper working at the highest temperature until these vessels are in equilibrium prior to discharging the liquid content to a flashtank. The present invention thereby meets an increasing need for optimization of energy consumption by achieving a lower steam consumption compared to the processes of the prior art, e.g. as exemplified by the processes described in WO/2011/006854.

SUMMARY OF THE INVENTION

As set out above, THP plants known from the prior art mostly has one preheating vessel and one flash vessel, and the substrate fed to the THP is about 5-30 C, most commonly about 15 C, unless a pre-heating system is used to pre-heat the feed to temperatures as high as 50 C. Flash steam from the steam explosion in the flashtank will, thus, normally heat the pulper to approximately 85-100 C, most commonly about 90 C.

Furthermore, the pulper is normally maintained at ambient pressure, wherefore feed temperatures higher than approximately 23-25 C, the specific temperature depending on the specific heat losses of the specific process, will result in boiling in the pulper and loss of thermal energy. Alternatively, both the pulper and flashtank is maintained at higher than ambient pressure to prevent boiling in the pulper, but this will also result in loss of thermal energy due to higher temperatures in the treated substrate discharged from the THP. In rare cases where large amounts of low temperature heat that otherwise would be wasted is available, it can be beneficial to use hot water to dilute biowaste such as food waste prior to treatment in a THP. To avoid the pulper from boiling, a cooler can be installed on the flashtank to reduce the amount of flash steam returned to the pulper. This makes it possible to benefit from lower substrate viscosity resulting from higher substrate temperature prior to THP treatment while preventing the pulper from boiling.

In contrast, the present invention makes use of at least two preheating vessels in series and two flash vessels in series for step-wise pre-heating and pressure reduction, respectively. The optimal temperature and pressures in these vessels depend on the temperature in the feed to the THP. Thus, with feed temperatures below about 50 C, 165 C in the reactor, a certain retention pressure, and about 3 meters submersion of flash steam lances in the pulper vessels, the pressure in both the second flashtank and first pulper will be maintained below ambient by using a vacuum system connected to the first pulper. The present invention, however, also contemplates processes in which the pressure in the first preheating vessels is below ambient pressure, whereas the pressure in the second preheating vessel is above ambient pressure. Thus, for instance the pressure of the second preheating vessel may be at 1.1 barA pressure, while the first preheating vessel may be at 0.8 barA pressure. Such a scenario would allow for feed temperatures somewhat above 50 C while still maintaining good use of the processes of the present invention. The vacuum system of the methods and plants of the present invention is, thus, essential for achieving decreased steam consumption by using two preheating vessels and two flash vessels in series. With substrate in the normal temperature range (10-30 C), the first preheating vessel is maintained well below ambient pressure to allow transfer of low temperature steam from the second flash vessels to the first preheating vessel. This is performed while controlling the pressure in both preheating vessels to prevent boiling.

Flashsteam is typically injected below liquid level in both preheating vessels. This ensures that steam condenses in the liquid while other non-condensable gases travels through the liquid and enters the headspace. Injecting flash steam through carefully designed injection points contributes to mix the substrate during the preheating process. However, other means of steam injection such as mechanical mixing is also possible. Such methods e.g. rely on steam injection into the piping followed by mechanical mixers to ensure complete condensation of all steam. As the later systems are, however, known to be prone to leakage, wear and tear, and given the presence of H2S and thiols, the former method relying on flashsteam injection below liquid level in the pulpers is preferred. Temperature and pressure transmitters are used to calculate the partial pressure of steam and other non-condensable gases in the headspace of the preheating vessels. Input from these instruments are used to control a valve that releases gases out from the vessels. Gases from the second (hot) preheating vessel is vented to below liquid level in the first (cold) preheating vessel. This ensures that steam carried with the process gas is used for pre-heating in the first vessel. The partial pressure of non-condensable gases in the first preheating vessel will be maintained at a desired level. The desired partial pressure of non-condensable gases in the headspace of the first preheating vessel will depend on the specific substrate used and feed temperature. With lower total pressure in the pre-heating vessel, more flash steam is recovered from the connected flashtank, while more heat is lost to the vacuum system since the ratio between steam and non-condensable gases increases. Measurements on the amount of non-condensable gases released from different feedstocks during THP treatment shows that the optimum volume percent non-condensable gases in most cases will be between 10 to 35%. At this optimum, the derivative is zero for a function describing the heat loss to the vacuum system and energy recovered from the connected flashtank. Models simulating the process and working with real time data from the applicable plant can be used to adjust process setpoints continuously to ensure optimal plant performance.

It is therefore an objective of the present invention to provide processes and plants that, in the context of processes involving THP and steam explosion, enables optimization of steam consumption by achieving a lower steam consumption compared to the processes of the prior art It is yet another object of the present invention to provide processes and plants that, in the context of processes involving THP and steam explosion, enables optimization of steam consumption by achieving a lower steam consumption compared to the processes of the prior art, and which are simple and easy to integrate into existing wastewater treatment plants by retrofitting.

Finally, it is an objective of the present invention by using the methods of the present invention as an add-on by retrofitting to any thermal hydrolysis process with a cold feed and a warm discharged liquid. Thus, the methods of the present invention could be combined with the processes described in e.g. WO/2011/006854 and WO/2014/123426 and other similar thermal hydrolysis processes with the aim to improve heat recovery and reduce overall energy consumption.

These and other objectives are solved by the present invention.

Accordingly, in a first aspect of the invention, there is provided a method for hydrolysis of a liquid substrate, having a dry solids content of between 2 and 30%, preferably between 14 and 20%, and a temperature of 10 to 30 C which liquid substrate is to be used in an anaerobic fermentation, digestion or another process aimed at producing or extracting methane or other valuable substances characterized in that:
  a) said liquid substrate is transferred to and preheated and mixed in a first pulper, which is operated at a temperature of 40 C to 90 C and at a pressure of 0.2 to 0.9 barA, by injection of flash steam from a downstream flashtank
  b) said pressure of 0.2 to 0.9 barA, under which said first pulper is being operated, is being maintained by a vacuum system working, to maximize the condensation of any condensable vapors that are not condensed when passing through said liquid substrate in said first pulper
  c) said vacuum system further being capable of maximizing the compression of any remaining non-condensable vapors and being connected to an injection unit that is capable of injecting said non-condensable vapors into a downstream anaerobic digester, fermenter or any other process gas treatment system
  d) said preheated liquid substrate is transferred from said first pulper to a second pulper, which is operated at a temperature of 90 C to 135 C and at a pressure of 0.7 to 3.3 barA, and wherein said liquid substrate is subjected to further mixing and pre-heating, by injection of flash steam from a downstream flashtank
  e) said further preheated liquid substrate is transferred from said second pulper to one or more reactors working in parallel or series wherein said liquid substrate is heated to temperatures in the range of 140 C to 180 C and at a pressure of 3.6 to 10 barA
  f) said liquid substrate is transferred from said one or more reactors working in series or parallel to a first flashtank operated at a temperature of 100 C to 140 C and at a pressure of 1 to 3.6 barA whereby a pressure reduction occurs, and wherefrom flash steam resulting from said pressure reduction is transferred to said second pulper operated at a temperature of 90 C to 135 C and at a pressure of 0.7 to 3.3 barA
  g) said liquid material is transferred from said first flashtank to a second flashtank operated at a temperature of 70 C to 100 C and at a pressure of 0.35 to 1 barA, whereby a further pressure reduction occurs, and wherefrom flash steam resulting from said further pressure reduction in said second flashtank is transferred to said first pulper operated at a temperature of 40 C to 90 C and at a pressure of 0.2 to 0.9 barA by means of said vacuum system.

This method enhances and/or optimizes steam consumption by achieving a lower steam consumption compared to the processes of the prior art. With regards the temperatures and pressures set out under a), b), d), e) and f) above, the skilled person will readily appreciate that in an ideal scenario the partial pressure of steam at e.g. 40 C, 90 C and 140 C will be 0.07 barA, 0.7 barA and 3.6 barA, respectively. Similarly, in an ideal scenario the partial pressure of steam is 3.3 barA at 137 C, not 135 C. That is to say, the temperatures and pressures set out do not follow the saturation line for steam. However, as the processes and methods of the present invention will in many embodiments also involve the presence other non-condensable gases, the pressures and temperatures set out under a), b), d), e) and f) above have to a certain extent been rounded off, in order to also take the possible presence of any such other non-condensable gases into account.

In an embodiment of the first aspect of the invention, said method is further characterized in that an interconnected vapor cooler works to remove any vapors condensable below the working temperature of said first pulper and that said vacuum system works to maximize the condensation of any condensable vapors that are neither condensed when passing through said liquid substrate in said first pulper nor in said interconnected vapor cooler.

This embodiment further enhances and/or optimizes steam consumption by achieving a lower steam consumption compared to the processes of the prior art In a second aspect of the invention, there is provided a plant for hydrolysis of a liquid substrate, having a dry solids content of between 2 and 30%, preferably between 14 and 20%, and a temperature of 10 to 30 C which liquid substrate is to be used in an anaerobic fermentation, digestion or another process aimed at producing or extracting methane or other valuable substances, said plant comprising:
  a) a first pulper for mixing and preheating said liquid substrate, to which said liquid substrate is transferred and which is operated at a temperature of 40 C to 90 C and at a pressure of 0.2 to 0.9 barA, by injection of flash steam from a downstream flashtank
  b) a vacuum system for maintaining said pressure of 0.2 to 0.9 barA, under which said first pulper is being operated, which vacuum system works to
    maximize the condensation of any condensable vapors that are not condensed when passing through said liquid substrate in said first pulper, and
    maximize the compression of any remaining non-condensable vapors and remaining condensable vapors.
  c) an injection unit that is capable of injecting said non-condensable vapors into a downstream anaerobic digester or a process gas treatment device being connected to said vacuum system d) a second pulper, which is operated at a temperature of 90 C to 135 C and at a pressure of 0.7 to 3.3 barA, to which said preheated liquid substrate is transferred from said first pulper, and wherein said liquid substrate is subjected to further mixing and pre-heating, by injection of flash steam from a downstream flashtank e) one or more reactors working in parallel or series to which said further preheated liquid substrate is transferred from said second pulper, and wherein said liquid substrate is heated to temperatures in the range of 140 C to 180 C and at a pressure of 3.6 to 10 barA f) a first flashtank, to which said liquid substrate is transferred from said one or more reactors working in series or parallel, said first flashtank being operated at a temperature of 100 C to 140 C and at a pressure of 1 to 3.6 barA whereby a pressure reduction occurs, and wherefrom flash steam resulting from said pressure reduction is transferred to said second pulper operated at a temperature of 90 C to 135 C and at a pressure of 0.7 to 3.3 barA g) a second flashtank, to which said liquid material is transferred from said first flashtank, said second flashtank being operated at a temperature of 70 C to 100 C and at a pressure of 0.3 to 1 barA, whereby a further pressure reduction occurs, and wherefrom flash steam resulting from said further pressure reduction in said second flashtank is transferred to said first pulper operated at a temperature of 40 C to 90 C and at a pressure of 0.2 to 0.9 barA by means of said vacuum system.

This plant enhances and/or optimizes steam consumption by achieving a lower steam consumption compared to the processes of the prior art. As regards the temperatures and pressures set out under a), b), d), e) and f) above, the skilled person will readily appreciate that in an ideal scenario the partial pressure of steam at, e.g. 40 C, 90 C and 140 C will be 0.07 barA, 0.7 barA and 3.6 barA, respectively. Similarly, in an ideal scenario the partial pressure of steam is 3.3 barA at 137 C, not 135 C. That is to say, the temperatures and pressures set out do not follow the saturation line for steam. However, as the processes and methods of the present invention will in many embodiments also involve the presence other non-condensable gases, the pressures and temperatures set out under a), b), d), e) and f) above have to a certain extent been rounded off, in order to also take the possible presence of any such other non-condensable gases into account.

In an embodiment of the second aspect of the invention, the plant further comprises an interconnected vapor cooler working to remove any vapors condensable below the working temperature of said first pulper, wherein said vacuum system works to maximize the condensation of any condensable vapors that are neither condensed when passing through said liquid substrate in said first pulper nor in said interconnected vapor cooler working to remove any vapors condensable below the working temperature of said first pulper, and maximize the compression of any remaining non-condensable vapors This embodiment further enhances and/or optimizes steam consumption by achieving a lower steam consumption compared to the processes of the prior art Any of the embodiments of the first aspect of the invention may be combined with any of the embodiments of the second aspect.

In a third aspect of the invention, there is provided a method for retrofitting an existing plant for thermal hydrolysis of a liquid substrate, having a dry solids content of between 2 and 30%, preferably between 14 and 20%, and a temperature of 10 to 30 C which liquid substrate is to be used in an anaerobic fermentation, digestion or another process aimed at producing or extracting methane or other valuable substances, whereby said retrofitting ensures that said plant comprises at least the following;

a) a first pulper for mixing end preheating said liquid substrate, to which said liquid substrate is transferred and which is operated at a temperature of 40 C to 90 C and at a pressure of 02 to 0.9 barA, by injection of flash steam from a downstream flashtank b) a vacuum system for maintaining said pressure of 0.2 to 0.9 barA, under which said first pulper is being operated, which vacuum system works to maximize the condensation of any condensable vapors that are not condensed when passing through said liquid substrate in said first pulper, and maximize the compression of any remaining non-condensable vapors c) an injection unit that is capable of injecting said non-condensable vapors into a downstream anaerobic digester or a process gas treatment device being connected to said vacuum system d) a second pulper, which is operated at a temperature of 90 C to 135 C and at a pressure of 0.7 to 3.3 barA, to which said preheated liquid substrate is transferred from said first pulper, and wherein said liquid substrate is subjected to further mixing and pre-heating, by injection of flash steam from a downstream flashtank e) one or more reactors working in parallel or series to which said further preheated liquid substrate is transferred from said second pulper, and wherein said liquid substrate is heated to temperatures in the range of 140 C to 180 C and at a pressure of 3.6 to 10 barA f) a first flashtank, to which said liquid substrate is transferred from said one or more reactors working in series or parallel, said first flashtank being operated at a temperature of 100 C to 140 C and at a pressure of 1 to 3.6 barA whereby a pressure reduction occurs, and wherefrom flash steam resulting from said pressure reduction is transferred to said second pulper operated at a temperature of 90 C to 135 C and at a pressure of 0.7 to 3.3 barA g) a second flashtank, to which said liquid material is transferred from said first flashtank, said second flashtank being operated at a temperature of 70 C to 100 C and at a pressure of 0.3 to 1 barA, whereby a further pressure reduction occurs, and wherefrom flash steam resulting from said further pressure reduction in said second flashtank is transferred to said first pulper operated at a temperature of 40 C to 90 C and at a pressure of 0.2 to 0.9 barA by means of said vacuum system.

This method for retrofitting enhances and/or optimizes steam consumption by achieving a lower steam consumption compared to the processes of the prior art. As regards the temperatures and pressures set out under a), b), d), e) and f) above, the skilled person will readily appreciate that in an ideal scenario the partial pressure of steam at e.g. 40 C, 90 C and 140 C will be 0.07 barA, 0.7 barA and 3.6 barA, respectively. Similarly, in an ideal scenario the partial pressure of steam is 3.3 barA at 137 C, not 135 C. That is to say, the temperatures and pressures set out do not follow the saturation line for steam. However, as the processes and methods of the present invention will in many embodiments also involve the presence other non-condensable gases, the pressures and temperatures set out under a), b), d), e) and f) above have to a certain extent been rounded off, in order to also take the possible presence of any such other non-condensable gases into account.

In an embodiment of the third aspect of the invention, the method for retrofitting further comprises ensuring that said plant comprises an interconnected vapor cooler working to remove any vapors condensable below the working temperature of said first pulper, and that said vacuum system works to:

maximize the condensation of any condensable vapors that are neither condensed when passing through said liquid substrate in said first pulper nor in said interconnected vapor cooler working to remove any vapors condensable below the working temperature of said first pulper, and maximize the compression of any remaining non-condensable vapors This method for retrofitting further enhances and/or optimizes steam consumption by achieving a lower steam consumption compared to the processes of the prior art.

Any of the embodiments of the first aspect and second aspect of the invention may be combined with any of the embodiments of the third aspect.

DETAILED DESCRIPTION

Below the present invention will be described in further detail with reference to the nomenclature also used in the accompanying FIGS. 1-4.

The present invention, relates to methods and plants employing Thermal Hydrolysis Processes (THP) in combination with steam explosion, which make use of pulpers and flashtanks for pre-heating and pressure reduction, respectively. The present invention also relates to methods for retrofitting existing plants employing Thermal Hydrolysis Processes (THP).

As already noted above, the present invention makes use of vacuum in combination with at least two pulpers and two flashtanks in series for step-wise pre-heating and pressure reduction, respectively.

The optimal temperature and pressures in the individual vessels in a method or plant according to the present invention will depend on the temperature in the feed to the THP. With feed temperatures below about 50 C, the pressure in the second flashtank and first pulper will be maintained below ambient by using a vacuum system connected to the first pulper. Typically, the temperature in the feed to a THP is approximately 15 C, and the normal range is from 10 to 30 C, such as 15-25 C. This makes the vacuum system essential for achieving decreased steam consumption by using two pulpers and two flashtanks. With substrate in the normal temperature range, the first pulper is maintained well below ambient pressure to allow transfer of low temperature steam from the second flashtank to the first pulper. This is performed while controlling the pressure in both pulper vessels to prevent boiling.

Flashsteam is preferably injected below liquid level in both pulpers. This ensures that steam condenses in the liquid while other non-condensable gases travels through the liquid and enters the headspace. Temperature and pressure transmitters are used to calculate the partial pressure of steam and other non-condensable gases in the headspace of the pulper vessels. Input from these instruments are used to control a valve that releases gases out from the vessels. Gases from the second (relatively hot) pulper is vented to below liquid level in the first (relatively cold) pulper. This ensures that steam carried with the process gas is used for pre-heating in the first pulper. The partial pressure of non-condensable gases in the first pulper will be maintained at a desired level. The optimal partial pressure of non-condensable gases in the headspace of the first pulper will depend on the specific substrate used.

Typically, the temperature of the liquid substrate fed to the first pulper in a method or plant according to the present invention will be in the range from 10 to 30 C, such as 15-25 C, e.g. 20-25 C, and the hydrolysis temperature applied in the one or more reactors working in parallel or series downstream of the second pulper will be in the range between 140 to 180 C, such as 155-165 C, e.g. app 160 C depending on ambient temperature and feedstock.

As is evident from the above, it is a particularly preferred embodiment of the present invention, to provide methods and plants (new or retrofitted) relying on a system with two pulpers and two flashtanks wherein the first pulper is connected to a vacuum system. The skilled person will, however, readily realize that certain other embodiments, characterized by the same technical features, can easily be obtained by minor changes to the preferred methods and plants (new or retrofitted) of the present invention, i.e. those relying on a system with two pulpers and two flashtanks wherein the first pulper is connected to a vacuum system. Some of these additional embodiments, also falling within the present invention, will be explained in somewhat further detail below.

A first additional embodiment is a system relying on two pulpers but only one flashtank for achieving equally low steam consumption as described in the preferred embodiment above relying on a system with two pulpers and two flashtanks wherein the first pulper is connected to a vacuum system. This requires that the first pulper is connected to a vacuum system, and that a line connecting the headspace of the reactors) to the second pulper is used to depressurize the reactor(s) until the reactor(s) and second pulper are in equilibrium prior to transferring the liquid substrate from the reactor(s) to the flashtank. In such a system it is possible to operate with one less flashtank than the number of pulpers since the reactor(s) will play a similar role as the first flashtank in a system with an even number of pulpers and flashtanks, where the liquid substrate is transferred from the reactor(s) at maximum pressure. In such a system, the liquid substrate in the reactor(s) will boil as steam is transferred from the reactor to pre-heat substrate in a pulper. Thus, to prevent liquid from entering the flash steam system, it is important that the headspace volume in the reactor(s) in such a system is large and that steam transfer rates are low. The large headspace volume required results in less efficient use of the available reactor(s) volume and the low steam transfer rates increases the cycle time for each reactor. Both these effects reduce the capacity of the system. Because of this, it is more efficient to use even numbers of pulpers and flashtanks and to discharge substrate from reactors at maximum pressure.

Increasing the number of flashing stages will result in a lower overall steam consumption. In a process relying on a) a feed with 15 C and 16.5% dry solids content, b) all injection points for flash steam submerged 2 meters below liquid level, c) 165 C reactor temperature, d) non-condensable gases contributing with 0.1 bar partial in the first pulper and e) no heat losses to the surroundings, the overall steam consumption will be approximately 530 kg steam per ton of dry solids treated if three flashing stages are used. In comparison, processes with two flashing stages or one flashing stage will consume 640 and 900 kg saturated steam at 14 barA pressure per ton dry solids treated, respectively. For a process at similar conditions as those described above, the temperature will be approximately 43 C in the first pulper if three flashing stages are used and 64 C if two flashing stages are used.

The viscosity of most liquid substrates decreases with increasing temperature and increases with increasing dry solids content. For e.g. substrates such as sludge from waste water treatment plants, the viscosity is normally greatly reduced by heating the material from ambient temperatures to approximately 60 C. Viscosity continues to decrease by heating to higher temperatures, but to a somewhat smaller extent. With low temperature in the first pulper it can become necessary to operate the process with lower dry solids content in the feed to keep the viscosity at a manageable level. With similar process conditions as those described above, processes with two or three flashing stages will have equal steam consumption per ton dry solids treated if the dry solids content in the feed is 13.8% and 16.5%, respectively. Because of this, the benefit from using three flashing stages can be lost if it becomes necessary to reduce the dry solids content in the feed to keep the viscosity at a manageable level.

Also, as the skilled person would know, it is possible to pre-heat the incoming liquid substrate by using hot water for dilution, heat exchangers or the like. In such situations, i.e. if both the temperature of the liquid substrate feed to the first pulper and the hydrolysis temperature applied in the one or more reactors working in parallel or series downstream of the second pulper is sufficiently high, the working pressure of the first pulper will typically be more than 1 barA. One example of this would be a process, in which the liquid substrate is pre-heated to a temperature of 40 C, with small amounts of non-condensable gases, and where the hydrolysis is performed at a temperature of 220 C (and 23.2 barA). In this case, the first pulper will typically be run at 115 C and about 1.8 barA. Also in an embodiment relying on such operational conditions it is immediately apparent to the skilled person that at least some of the advantages of the present invention would still be obtained. Thus, the present invention would also be relevant to methods and/or plants relying on two pulpers and two flashtanks in series and feed having temperatures high enough to result in the first pulper being run above ambient pressure. Another example of such a method and/or plant would be a method/plant relying on feed having a temperature of about 65-70 C and a reactor retention pressure about 7 barA. Furthermore, in such a scenario it might be beneficial to use three pulpers and three flashtanks in series, rather than two of each, since this would, also in such a situation, make it possible to utilize steam below ambient pressure for pre-heating any incoming liquid substrate. The present invention would also be relevant to any such methods and/or plants.

However, in the majority of situations in a method or plant according to the present invention it will not be relevant to use more than two pulpers and two flashtanks in series since the liquid substrate temperature and the hydrolysis temperature will be lower than 40 C and 180 C, respectively.

In the prior art processes a conventional vacuum cooler would make use of a vacuum compressor to create a vacuum downstream a condensing cooler. The condenser cooler would then remove the condensable vapors so that the vacuum compressor would operate on remaining gases often referred to as non-condensable gases. In a method or plant according to the present invention the vacuum compressor does not have to treat all the vapors but only work on the non-condensable gases and thus have to perform a minimum of work. The condensing cooler for use in a method or plant according to the present invention can be designed in different ways, e.g. plate heat exchanger, tube heat exchanger vertical or horizontal, falling film or other solutions well known in condenser technologies such as vacuum evaporators. Common for these solutions is that a coolant needs to cool down the heat surfaces in order to indirectly cool and condense the vapors. Thus, the present invention to a large extent circumvents the need for a condensing cooler by making use of one or more additional pulpers enabling direct contact between cold substrate and condensable steam. Through this direct contact condensation inside a pulper, cold substrate is preheated without any heat surfaces that is known to be subject to scaling. The present invention moreover avoids problems with reduced heat transfer due to scaling in heat exchangers. Moreover, problems with heat transfer is minimalized as there are no heat surfaces. Additionally, the present invention minimizes the need for traditional coolers on warm hydrolyzed substrates prior to a fermentation process such as anaerobic digestion for methane production.

An important aspect of the present invention is to recover heat at temperatures that are lower compared to conditions, which existing THP plants operate at. It is crucial that all steam brought back to the pre-heating vessels condenses into the substrate that is to be pre-heated. This becomes extra challenging in the first pulper that operates at the lowest temperature because viscosity increases with decreasing temperatures. However, so-called steam tunneling, which is characterized by steam traveling from the injection point through the liquid surface, can be avoided by ensuring efficient mixing of the substrate in the pre-heating vessel. The density of steam decreases with decreasing pressure. As a result, the volume of steam transferred to the first pre-heating vessel will in most scenarios be large. This effect can be exploited and used to mix the substrate in the pre-heating vessel by injecting steam at carefully designed injection points. This makes it possible to treat highly viscous substrates with high dry solids content, such as above 10%, despite the lower temperatures compared to existing thermal hydrolysis processes. Efficient mixing is not only important for ensuring condensation of all steam returned to the pre-heating vessels, but also for homogenizing the substrate prior to further processing. Thus, homogenizing the substrate prior to treatment in the reactors also ensures a more complete hydrolysis. Condensation of $H_2O$ vapor into a cold substrate may cause severe vibrations due to implosions. The severity of implosions is a result of pressure and temperature in the vapor phase, as well as vapor bubble size, and temperature in the substrate. Large temperature difference and pressure difference causes the most violent vibrations. A normal method for reducing the temperature and pressure difference between vapor and liquid would be to reduce pressure in the vapors with a pressure reduction mechanism such as a pressure reduction valve, control valve or any other type of restriction that causes a pressure drop in the vapor feed line. The vapors that have been flashed off in the flashtank(s) will not be clean water vapor and contains components known to cause scaling and blockages in such restrictions. Instead a method or plant according to the present invention makes use of a vacuum compressor to lower the pressure and create a vacuum after the $H_2O$ vapors and the contaminants have been removed through condensation and injection through the pulper in direct contact with the cold substrate having a pH in the range of 3.5-8.5. A method or plant according to the present invention thereby reduces vapor pressure without such pressure reduction mechanisms taking place in the vapor phase and does this to such an extent that the pulper(s) can be operated at relatively low temperatures, typically 40-85° C., more typically 50-70° C., and even more typically in the range 58-68° C., with a minimum of vibrations and enabling a large degree of heat recovery. One example of a particular useful embodiment of a method or plant according to the present invention would be the processing of an alkaline substrate with a pH in the range of 7.0-8.5. Another example of a particular useful embodiment of a method or plant according to the present invention would be the processing of a substrate with a pH in the range of 3.5-7.0.

For most relevant substrates, viscosity increases with dry solid concentration, whereas viscosity decreases with increasing temperatures. The viscosity of raw substrates such as sludge is typically greatly reduced upon heating from ambient temperatures to about 60 to 65 C. Heating to even higher temperatures will lead to a further reduction in viscosity. The present invention enables operation at high dry solids concentration. As would be known by the skilled person, high dry solids concentrations will in itself contribute to reduced steam consumption in the magnitude of app. 10%-30% depending on substrate characteristics. In addition, a method or plant according to the present invention with two pulpers and two flashtanks decreases the overall steam consumption compared to prior art THP technology with 25-40% depending on the temperature in the feed to the THP.

A further preferred embodiment of the present invention is for the pulper(s) to include a steam introduction system that enables high intensity mixing by using voluminous vapors at vacuum conditions. This would introduce a further benefit of the present invention in that since the second pulper(s) would receive preheated feed at approx. 50-80 C more precisely 60-70 C, this would reduce the mixing requirements, and result in an reduced design volume compared to pulpers in conventional THP systems. Moreover, the need for mechanical mixing as such would be reduced. Whichever means of mixing are used in a certain embodiment, enhanced mixing can be achieved through an optimized orientation of the lances and through additional pumping. In a typical scenario, the first pulper will typically receive feed at about 15 C, which is heated to about 65 C. The second pulper will then receive feed at about 65 C which is then further heated to above 100 C A further particularly preferred embodiment of a method or plant according to the present invention comprises the use of pressure differences to move the liquid substrates both into the first pulper and between the different downstream vessels, i.e. so-called barometrical pumping. In certain embodiments barometrical pumping will be used in all steps involving a transfer of the liquid substrate into the first piper and between the different downstream vessels in other embodiments barometrical pumping will only be used in some of the steps involving a transfer of the liquid substrate into the first pulper and/or between the different downstream vessels. In the latter case, the transfer of the liquid substrate may, thus, also be achieved partly by ordinary pumps (centrifugal or progressive cavity pumps).

Figure 3:
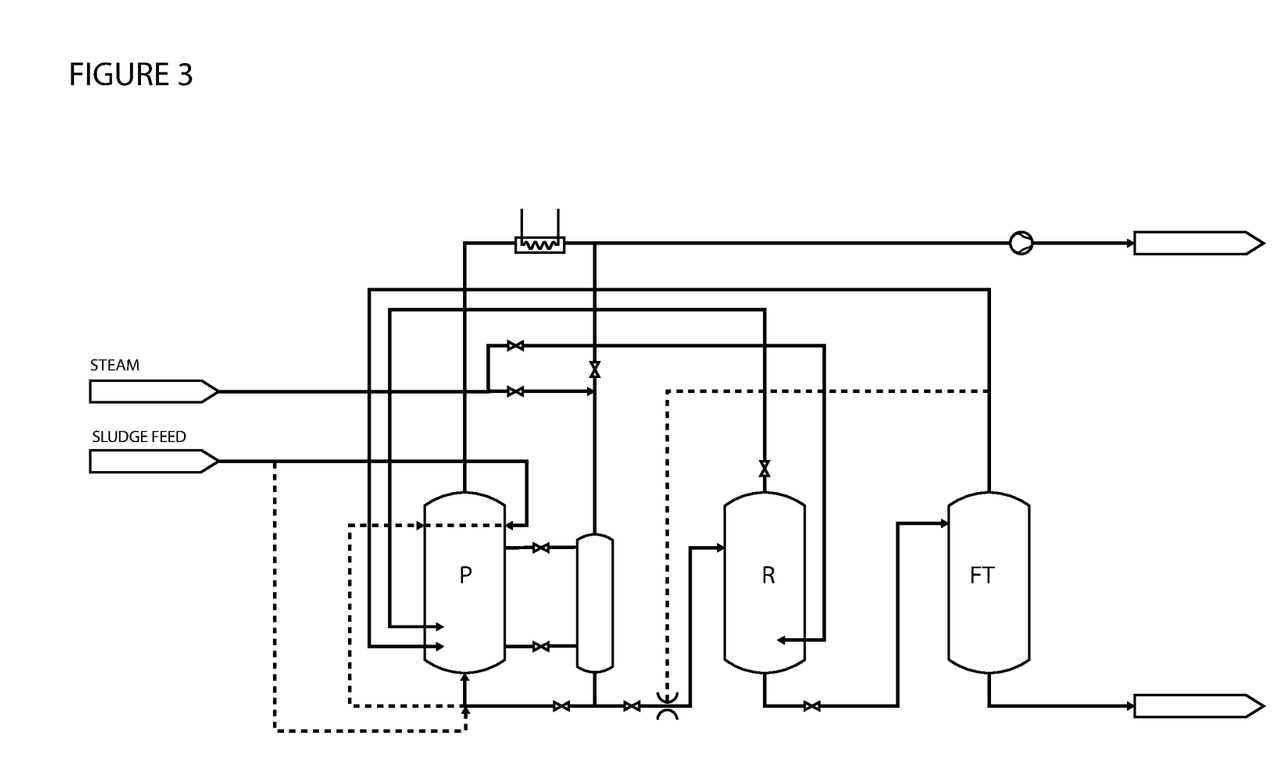
FIGS. 3 and 4 shows two different particularly preferred embodiments of a plant according to the present invention for performing a method according to the present invention, which makes use of barometrical pumping
Figure 4:
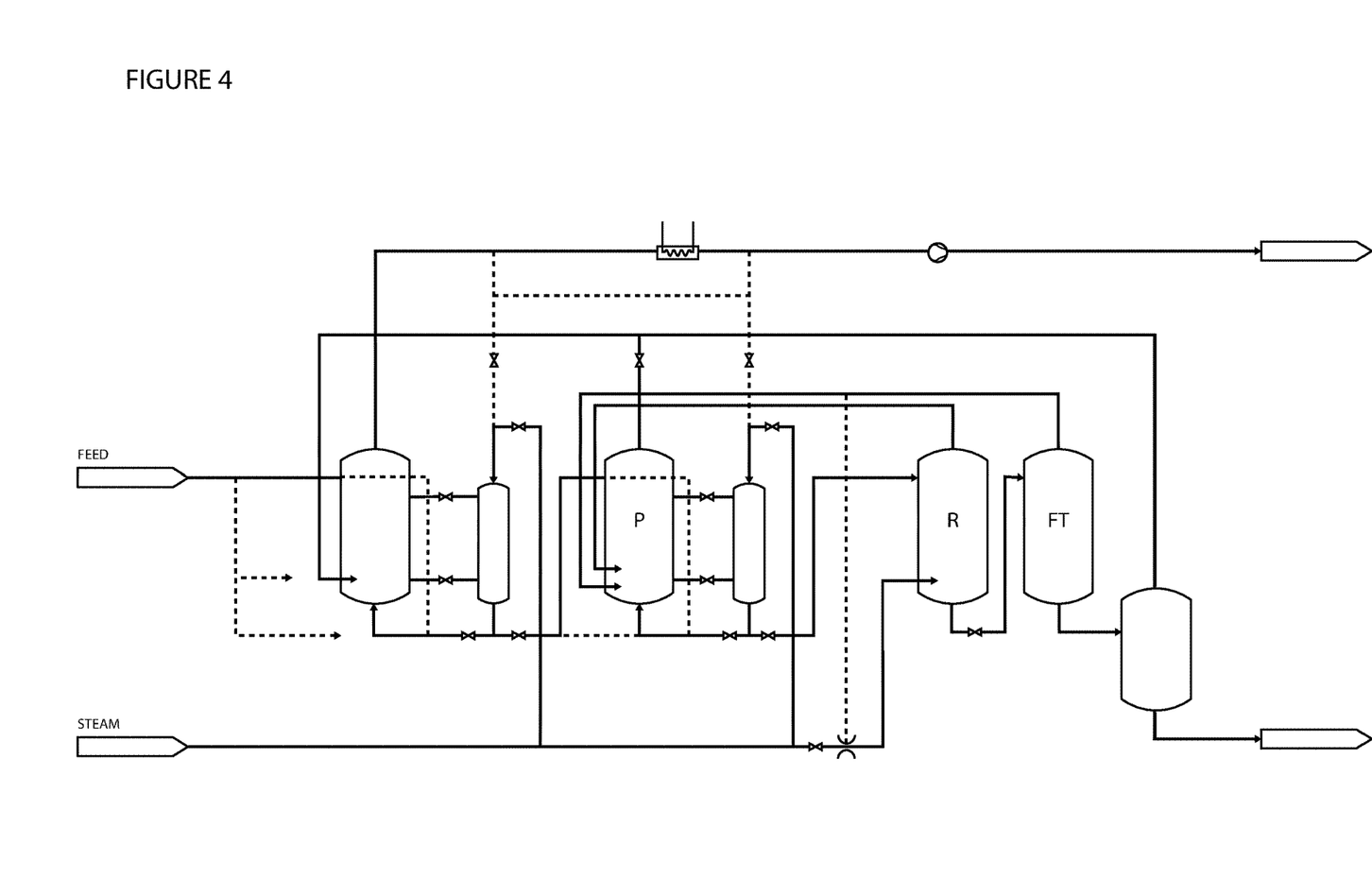

FIGS. 3 and 4 shows two such different particularly preferred embodiments of a system according to the present invention making use of barometrical pumping.

In the context of a method or plant according to the present invention barometrical pumping is to be understood as a pressurised first vessel used for pumping a substrate by means of a pressure difference. The first vessel is filled with the substrate that is to be pumped and is subsequently pressurized with a gas. This will result in the substrate being pressed out of the first vessel through piping in the bottom of the vessel if the piping is interconnected to a second vessel having a pressure below that of the first vessel. In a method or plant according to the present invention such a design will provide certain advantages compared to mechanical pumping.

The general pumping advantages of barometrical pumping would include:
a. No need for mechanical energy.
b. No movable parts are brought in contact with the substrate, which leads to lower wear and a reduced risk of leakage through sealings etc.
c. Relatively high pressures can easily be obtained (above 5 barA), which enables higher flow rates.

Additional Advantages of barometrical pumping regardless of the THP configuration would include:
a. In a batchwise THP, substrate is moved discontinuously between pressurised vessels. It is therefore no disadvantage that barometrical pumping can normally not produce a constant flow.
b. The volume of the pressurised vessel used for barometrical pumping may be equal to the desired reactor fill volume and thus a known volume is dosed to the reactor. This replaces instrumentation of THP to ensure correct reactor fill volume.
c. Steam used to pressurize the pressurised vessel used for barometrical pumping replaces steam in the downstream reactor(s). The consequence of this is that barometrical pumping upstream of the downstream reactor(s) does not affect the total steam consumption of a THP process.
d. It is advantageous with a large pulper volume to equalize temperature fluctuations. The volume of the pressurised vessel used for barometrical pumping can be considered as part of the pulper volume. The advantage of larger pulps is more stable temperature and increased residence time in pulses. Viscosity of substrates such as sludge is reduced with increasing residence time in pulper.
e. The capacity of THP plants increases because the reactor can be filled faster than what is possible with mechanical pumps used in existing THP processes
f. Higher flow rates that can be achieved with barometrical pumping, which makes it possible to mix the contents of the pulpers better. With a barometric egg you can achieve a powerful pulsing stirring that provides effective mixing and levelling of the temperature in the pulper.
g. THP processes are operated with liquids near the boiling point. Thus, cavitation on the suction side of pumps is a challenge. Barometrical pumping does not have the same challenges with cavitation as mechanical pumps.

h. By briefly connecting the pressurised vessel used for barometrical pumping to the vacuum system, the pressurised vessel will fill faster.

Advantages of barometrical pumping specifically for THP processes with two pulpers and two flash tanks would include:

a. It is challenging to find gaskets around rotary axes for pumps operated alternately at both lower and higher than ambient pressure at the center of the boiling point. Operating with, barometrical pumping, is less demanding as regards the quality of sealings, and the challenging operating conditions do thus not affect the overall cost of the system to a similar extent as would be the case with mechanical pumping.

b. With two pulpers, the temperature in the first pulper is low. With low temperature (first pulper), the viscosity is higher and a solution involving barometrical pumping is better suited to pump highly viscous substrates such as sludge.

c. With two-pulper system, the temperature is higher than in a regular system. It is challenging to find elastomers (used in positive displacement pumps) that tolerate the high temperatures in the second pulper (110 to 130 C). With barometrical pumping, this is not a challenge. This would introduce the further benefit of a lowered need for reactor feed pumps.

The present invention, thus, provides a method for continuous or batch hydrolysis of material by using stepwise pre-heating and cooling by using injection of flash steam and facilitating, steam flashing, respectively. Furthermore, at least one pre-heating vessel and at least one temperature reduction vessel is maintained below ambient pressure through interconnecting pipework. This allows transfer of flash steam at temperatures below 100 C to pre-heat incoming material in the pre-heating tank. In a particularly preferred embodiment of a method or plant according to the present invention the transfer of liquid substrate is achieved by barometrical pumping.

In short, a method according to the present invention can be characterized as follows:

a) A liquid substrate is transferred to and preheated by injection of flash steam in a pulper maintained below ambient pressure by use of a vacuum system.

b) The vacuum system comprise of any type of vacuum compressor or vacuum pump operating on the vapours that are not condensed when passing through the liquids in the preheating pulpers and a vapour cooler aimed at removing vapours below pulper temperature.

c) The vacuum system also compresses the non-condensable vapours and is connected to a unit that injects non-condensable gases into downstream anaerobic digesters or other biological treatment.

d) Transfer of substrate to a second pre-heating pulper maintained above ambient pressure.

e) One or more reactors where substrate is treated at temperatures in the range of 140 C to 220 C. In plants that operate in batch mode, the reactors can intermittently be placed under vacuum by using a line that connect the reactors to the pre-heating pulper that is maintained below ambient pressure. The second pre-heating pulper operates at higher pressure than ambient pressure. The higher pressure enables elevated temperatures inside the pulper, which results in reduced viscosity. The resulting pressure difference can at acceptable viscosity be used to transfer liquid material to the reactors without using pumps. However, it can be practical to use pumps to overcome pipe friction losses in case the viscosity of the substrate is too high. Instead of mechanical pumps, barometrical pumping is preferably used for pulper circulation and transfer of the substrate to the reactor.

f) After treatment in the reactor, the substrate is transferred to the first of two pressure-reduction flashtanks. Flash steam resulting from the decrease in pressure is transferred to the second of the two pre-heating pulpers which is maintained at ambient or higher pressure.

g) Substrate from the first pressure reduction flashtank is transferred to a second pressure reduction flashtank, which is maintained, below ambient pressure. Flash steam resulting from the pressure reduction in the second flashtank is transferred to the first pre-heating pulper which is maintained at lower than ambient pressure by using equipment for creating a vacuum.

Traditional equipment can be used to create a vacuum on the non-condensable gases and vapours to facilitate transfer of flash steam at lower than ambient pressure to the pre-heating pulper in a thermal hydrolysis process.

The vacuum system on the low-pressure pre-heating pulper can be connected to a unit that injects non-condensable gases to an anaerobic digester or other treatments of process gases.

In a further preferred embodiment of a method or a plant according to the present invention the voluminous low-pressure vapour bubbles are below atmospheric pressure reduced in size into small size bubbles in size in the range of 1-50 mm, preferably below 25 mm, more preferably below 10 mm in order to minimize vibrations and maximize heat recovery and mixing.

In yet a further preferred embodiment of a method or a plant according to the present invention both pre-heating pulpers may be equipped with pumps or agitators for further mixing in case of extraordinary high viscosity.

In yet a further preferred embodiment of a method or a plant according to the present invention both preheating pulpers are equipped with substrate outlet at an elevated level above the injection point of recycled flash steam from the first or second pressure reduction flashtank.

In yet a further preferred embodiment of a method or a plant according to the present invention the preheating pulpier feed is either introduced into the bottom of the preheating pulper, or above liquid level of the preheating pulper in combination with a substrate size reduction and distribution system that increases specific surface area of the cold substrate, or below liquid level of the preheating pulper in combination with a substrate size reduction and distribution system that increases specific surface area of the cold substrate.

In yet a further preferred embodiment of a method or a plant according to the present invention the content of inert gases inside the pulpers is controlled through control system by monitoring the temperature, pressure and opening the valves when a "false pressure" is calculated, that means deviating from the steam saturation line.

In yet a further preferred embodiment of a method or a plant according to the present invention a thermal mixing and transfer unit is used for transfer of substrate between the two pulpers, pulper a and pulper e, and may also be used for transfer from pulper e to the downstream reactor(s).

In a particularly preferred embodiment of a method or a plant according to the present invention such a thermal mixing and transfer unit may comprise A) a vessel having a fill volume used for transferring and filling the substrate into the reactor.
B) steam added to the top of the vessel to increase the pressure
C) valves for closing the feed from the pulper.
D) valves for distributing discharge to the next vessel.
E) valves for distributing the discharge to the bottom of the pulper for mixing the pulper
F) Means for bringing warm substrate from high level of the pulper above 50% fill level and more preferably above 60% fill level and even more preferable above 70% fill level to the colder substrate in the bottom of the pulper to mix the substrate without using pumps.

The reactors of a method or plant according to the present invention can be in series or in parallel.

In a particularly preferred embodiment of the present invention vacuum is created on the non-condensable gases after all condensable gases have first been condensed in a high temperature pulper for preheating of substrate, followed by a low temperature pulper for preheating of lower temperature substrate and (optionally) a vapour gas cooler in order to minimize the volume to create vacuum and compress non-condensable gases.

EXAMPLE 1

A plant according to a preferred embodiment of the present invention comprises at least two vacuum vessels one upstream the THP (pulper 1 (*a*)) and, one downstream the THP (flashtank 2 (*b*)). The two vessels are connected with a pipe from top of flashtank 2 (*b*) through lances distributed in piper 1 (*a*). A vacuum compressor (c) e.g. liquid ring compressor, connected to the headspace of the pulper 1 (*a*) will produce a vacuum in the head space of the piper. The work produced by the vacuum compressor will be made on the gases that are not condensed in the pulper 1 (*a*) and the subsequent condenser cooler (d). Flash steam from flashtank 2 (*b*) will be pulled through the pulper 1 (*a*) and condense as it enters the liquid phase in piper 1 (*a*) through the flash steam lances(s). The pulper 1 steam partial pressure will be around 0.2 bar, which means boiling point of approx. 60° C., while the total pressure might be somewhat higher due to the presence of other non-condensable gases. Some steam will follow the non-condensable gases and leave the pulper 1 (*a*) and will be condensed in a small condenser cooler upstream the vacuum compressor (c). This minimizes the required work to be made by the vacuum compressor (c) as it only has to work on the non-condensable gases.

Figure 1:
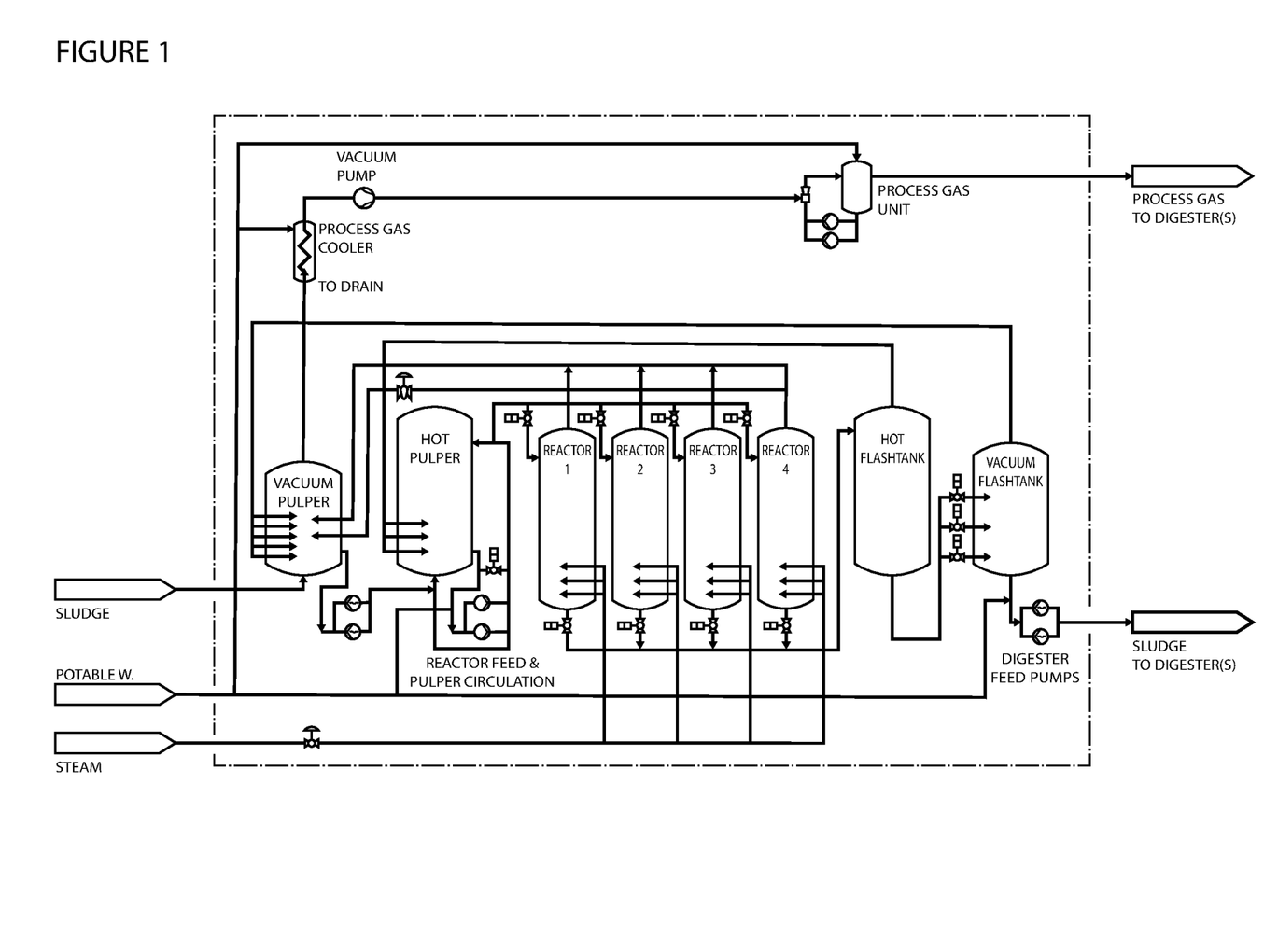
FIGS. 1 and 2 show two different embodiments of a plant according to the present invention for performing a method according to the present invention.
Figure 2:
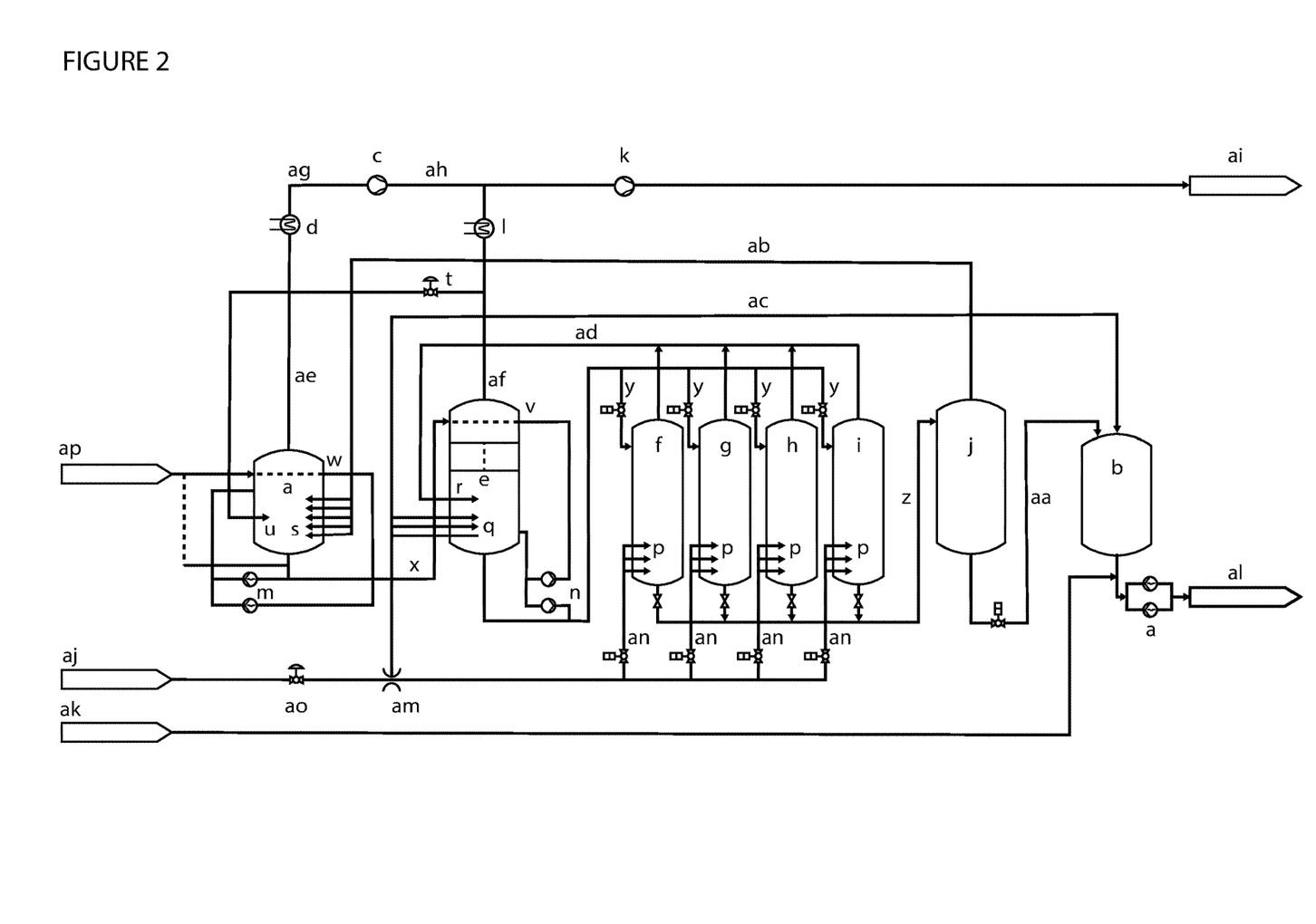

The two vessels (pulper 1 and flashtank 2) may be built on top of each other in order to achieve a compact and cost effective solution although it is not absolutely necessary. Moreover, by building on top of each other, important process advantages are enabled such as;

elevated flashtank 2 provide increased pressure at inlet on digester feed pumps (o) when located on floor level.
alternatively, elevated pulper 1 provides increased pressure at the inlet to the pumping system made to transfer substrate from piper 1 to pulper 2.
short distances and less pressure drop in connecting pipework FIGS. 1 and 2 indicate two different technical solutions with different degree of integration with the thermal hydrolysis process. FIG. 2 enables the use of vacuum in order to move substrate between the vessels and thus eliminate pumps. In case pumps are eliminated a thorough control with the pressure differences will be required. Moreover, steam lances need to be optimized for achieving well mixed pulper vessels. That apply to both pulper 1 (*a*) and pulper 2 (*e*). Reactor feed pumps (n) may also be eliminated Filling of reactors may also be eliminated if reactor head space is connected with the vacuum compressor (c) through a valve (t) in order to minimize pressure in the reactors during substrate filling time.

Substrate rheology is influenced by substrate temperature. Basically, viscosity decreases with increased temperature. A consequence of operating a plant according to the present invention is that high temperature material is fed to pulper 2 (*e*). The result of increased pulper 2 feed temperature will be increased temperature inside pulper 2 (*e*) during operation. At higher temperature the fluid will be easier to move between the vessels and shorter reactor (g) feed time can be achieved. As reactor feed time is a significant part of the THP total cycle time, the overall THP capacity will increase equivalently. Another benefit of operating at elevated temperatures will be easier mixing of pulper 2 (*e*).

Pulper 2 (*e*) is a continuous fed vessel with discontinuous discharge when feeding the reactors (g). The discontinuous discharge makes it necessary to allow for some variation of pulper 2 (*e*) level during a cycle.

Flashtank 1 (*j*) will operate at a slightly higher pressure than pulper 2 (*e*). The pressure difference will basically be determined by the elevation of the flash steam lances (q) in pulper 2 (*e*) and the pressure drop in the flash steam line (ac) and the flash steam lances (q).

Flashtank 2 (*b*) will operate at a slightly higher pressure than pulper 1 (*a*). The pressure difference will basically be determined by the elevation of the flash steam lances (s) in pulper 1 (*a*) and the pressure drop in the flash steam line (ab) and the flash steam lances (s).

EXAMPLE 2

In the present example, the additional pulper and flashtank required in a method or plant according to the present invention will be referred to as pulper a and flashtank b, respectively. A THP plant with the invention will also include pulper e and flashtank j that are similar to vessels in existing THP plants. The main process flows are shown in the figure below.

FIGS. 1 and 2 show two different embodiments of a system according to the present invention.

Pulper a

All lines for ventilation of non-condensable gases from pulper e will go to below liquid level in pulper a. Pulper a will be fitted with a vacuum pump and be at the lowest pressure in the system. The temperature and pressure in the headspace of pulper a will be measured to calculate the partial pressure of steam and other gases. The goal is to control the total pressure in pulper a to prevent the substrate from boiling while maintaining the concentration of non-condensable gases at a low level. There will be a line from the headspace of flashtank b to below liquid level in pulper a. This is to transfer flash steam to pre-heat the substrate in pulper a. During normal operation and with a pulper feed temperature below about 50 C, both pulper a and flashtank b are maintained below ambient pressure. The preheated substrate will be transferred from pulper a to pulper e. For low viscosity materials, pumps may be used. However, the risk of cavitation is significant and the elevation of the pumps critical. The problem becomes significant for high viscosity substrates. The invention includes a thermal transfer and mixing unit that will replace the pumps. However, any means for transferring substrate from pulper a to pulper e can be used without any negative impact on the overall process.

The thermal transfer and mixing unit will be a vessel that receives hot substrate from pulper a. Because cold substrate has higher specific density than warm substrate, the warmest substrate will be found in the top section of the pulpers. Of that reason the outlet from pulper a to the thermal transfer and mixing unit is at a high level in the pulper just below maximum liquid level. The warm substrate will flow over to the thermal transfer and mixing unit. Once the mixing unit is filled, the vessel can be closed and steam added to the top for pressurization. Once pressurized, the warm substrate can be transferred to selected reactor. The warm substrate can also be recycled back to the pulper a for mixing the pulper.

The thermal transfer and mixing unit may have a second inlet from a lower pulper level to enable filling even though pulper is not filled up and in order to enable mixing at a lower level without filling the thermal transfer and mixing unit to max level.

The thermal transfer and mixing unit has a known volume that will be used for flow control when filling the reactors through batching into the reactor.

Pulper e

All lines for ventilation of non-condensable gases from reactors will go to below liquid level in pulper e. Pulper e will receive substrate from pulper a and flashsteam from flashtank j. Substrate pre-heated in pulper a will be fed to reactors. The temperature and pressure in the headspace of pulper e will be measured to calculate the partial pressure of steam and other gases. A line is installed to ventilate gases from the headspace of pulper e to below liquid level in pulper a. The goal is to control the total pressure in pulper e to prevent boiling while maintaining the concentration of other gases at a low level. The temperature and pressure in pulper e will depend on the temperature of the feed to pulper a and the selected reactor temperature. However, during normal operation the temperature will be well above 100 C and the total pressure will be above ambient.

In a batch process, the total pressure in the reactors can be reduced to below ambient pressure prior to receiving substrate from pulper e. This is done with ventilation lines from the headspace of the reactors to below liquid level in pulper a. The resulting pressure difference between pulper e and the reactors can be used to transfer liquid substrate to the reactors without using pumps. If required, and the reactor cycle times allows for it, the headspace of pulper e can be pressurized with steam to increase the pressure difference between pulper e and the reactor receiving liquid substrate to facilitate reactor filling. If it is desired, pumps can be used for reactor filling with no negative impact on the rest of the process. Instead of normal pumps, a barometric egg can also be used for circulation of the pulper and reactor feeding, e.g. with one barometric egg fitted on each pulper. In such a scenario valves will control if the barometric egg feeds the reactors or recycle substrate back to the pulper for mixing. During filling of the barometric egg, the headspace of the barometric egg can be connected to the vacuum system to speed up the filling rate. The headspace in the barometric egg will be pressurized by steam for discharging the content to the reactors or for circulating back to the pulper for mixing purposes. The sequence of filling the barometric egg, mixing pulper and feeding of reactor(s) will be a sequential stepwise process.

During startup or other out of the ordinary situations, it may be necessary to either pre-heat the liquid substrate in pulper e or pressurize the headspace of the vessel to transfer substrate to the reactors. For this reason, it can be beneficial to prepare pulper e for live steam injection below and above liquid level.

Reactors f, g, h, i

The reactors are equipped with steam lances for injection of live steam into the liquid substrate. Furthermore, they are equipped with a valve and a line to ventilate gas from the headspace to pulper a. This same line can be used to place the reactors at below ambient pressure prior to reactor filling.

Overall Performance

The actual steam consumption, temperatures and pressures depend on several factors. Some of these are temperature and composition of the feed, selected reactor temperature and pressure, liquid level above pulper steam lances, pressure losses in piping, loss of heat to surroundings and dynamic effects. However, the overall performance can be calculated with sufficient accuracy.

In the table below, typical vessel temperatures and pressures are given as approximate values. As basis for the calculation, it is assumed 16.5% dry solids content in the feed, 5, 15 and 40 C feed temperature and 140, 165 and 220 C reactor temperature.

Typical pressure losses in piping, influence of non-condensable gases and hydraulic pressures at steam injection points are included in the calculations. With lower losses the temperatures and pressures in pulper 1 and 2 will be somewhat higher while the temperatures and pressures in flashtank 1 and 2 will be lower. With higher losses, the temperatures and pressures in pulper 1 and 2 will be somewhat lower while temperatures and pressures in flashtank 1 and 2 will be somewhat higher. Furthermore, steam can be released from pulper 2 to pulper 1 to heat pulper 1 to higher temperatures if this is desired. This will influence temperatures and pressures in other vessels. The numbers presented below are examples of realistic average temperatures and pressures while the plant is in steady state operation. Please note that indicated pressures includes the presence of non-condensable gases and that temperatures are rounded off to the closest whole number while pressures are rounded off to include only one decimal number.

| Vessel | Feed temperature [C.] | Hydrolysis temperature [C.] | Vessel temperature [C.] | Vessel pressure [barA] |
|---|---|---|---|---|
| Pulper a (1) | 5 | 140 | 40 | 0.2 |
| Pulper e (2) | | | 90 | 0,7 |
| Reactors f, g, h, i | | | 140 | 3.7 |
| Flashtank j (1) | | | 100 | 1.0 |
| Flashtank b (2) | | | 72 | 0.4 |
| Pulper a (1) | 15 | 140 | 49 | 0.2 |
| Pulper e (2) | | | 94 | 0. |
| Reactors f, g, h, i | | | 140 | 3.7 |
| Flashtank j (1) | | | 103 | 1.1 |
| Flashtank b (2) | | | 75 | 0.4 |
| Pulper a (1) | 40 | 140 | 69 | 0.4 |
| Pulper e (2) | | | 103 | 1.1 |
| Reactors f, g, h, i | | | 140 | 3.7 |
| Flashtank j (1) | | | 111 | 1.5 |
| Flashtank b (2) | | | 86 | 0.6 |

-continued

| Vessel | Feed temperature [C.] | Hydrolysis temperature [C.] | Vessel temperature [C.] | Vessel pressure [barA] |
|---|---|---|---|---|
| Pulper a (1) | 5 | 165 | 57 | 0.3 |
| Pulper e (2) | | | 113 | 1.6 |
| Reactors f, g, h, i | | | 165 | 7.0 |
| Flashtank j (1) | | | 119 | 1.9 |
| Flashtank b (2) | | | 78 | 0.5 |
| Pulper a (1) | 15 | 165 | 64 | 0.3 |
| Pulper e (2) | | | 116 | 1.8 |
| Reactors f, g, h, i | | | 165 | 7.0 |
| Flashtank j (1) | | | 122 | 2.1 |
| Flashtank b (2) | | | 83 | 0.5 |
| Pulper a (1) | 40 | 165 | 82 | 0.6 |
| Pulper e (2) | | | 125 | 2.3 |
| Reactors f, g, h, i | | | 165 | 7.0 |
| Flashtank j (1) | | | 129 | 2.6 |
| Flashtank b (2) | | | 94 | 0.8 |
| Pulper a (1) | 5 | 180 | 66 | 0.4 |
| Pulper e (2) | | | 127 | 2.5 |
| Reactors f, g, h, i | | | 180 | 10 |
| Flashtank j (1) | | | 131 | 2.8 |
| Flashtank b (2) | | | 84 | 0.6 |
| Pulper a (1) | 15 | 180 | 74 | 0.5 |
| Pulper e (2) | | | 131 | 2.8 |
| Reactors f, g, h, i | | | 180 | 10 |
| Flashtank j (1) | | | 134 | 3 |
| Flashtank b (2) | | | 88 | 0.7 |
| Pulper a (1) | 40 | 180 | 89 | 0.8 |
| Pulper e (2) | | | 137 | 3.3 |
| Reactors f, g, h, i | | | 180 | 10 |
| Flashtank j (1) | | | 140 | 3.6 |
| Flashtank b (2) | | | 100 | 1 |
| Pulper a (1) | 5 | 220 | 95 | 1 |
| Pulper e (2) | | | 167 | 7.3 |
| Reactors f, g | | | 220 | 23.2 |
| Flashtank j | | | 168 | 7.6 |
| Flashtank b (2) | | | 103 | 1.1 |
| Pulper a (1) | 15 | 220 | 100 | 1.1 |
| Pulper e (2) | | | 168 | 7.6 |
| Reactors f, g, h, i | | | 220 | 23.2 |
| Flashtank j (1) | | | 170 | 7.9 |
| Flashtank b (2) | | | 108 | 1.3 |
| Pulper a (1) | 40 | 220 | 115 | 1.8 |
| Pulper e (2) | | | 174 | 8.7 |
| Reactors f, g, h, i | | | 220 | 23.2 |
| Flashtank j (1) | | | 9 | 176 |
| Flashtank b (2) | | | 119 | 2.0 |

With the most typical conditions, which is 15 C feed temperature and 165 C reactor temperature the overall steam consumption will be approximately 640 or 100 reported as kg/tDS or kg/m3 feed, respectively. This is lower than any other existing thermal hydrolysis processes with steam explosion that utilize live steam injection for heat transfer. The low steam consumption is made possible by using flash steam below ambient pressure for pre-heating. Furthermore, using pressure differences or a barometric egg instead of pumps for reactor filling facilitates shorter filling times. In addition, pre-heating to higher temperatures reduces steam injection time in the reactors. These two factors contribute to increase the capacity per reactor volume compared to existing THP plants.

EXAMPLE 3

In most jurisdictions around the world, a plant or system comprising pressure vessels needs to be inspected on a regular basis, e.g. on annual basis, as part of the certification of the industrial facilities (e.g. a plant or system according to the present invention) comprising pressure vessels. National or regional regulations may regulate the specific inspection frequency required. As a consequence of the time required for such inspections, a plant according to the present invention as described in examples 1 and 2 will be subjected to certain down-time periods leading to a reduced capability to process liquid substrates. In such situations the stable plant operation of a plant or a system according to either of examples 1 or 2 above can be achieved by a) implementing additional elements/features allowing for the safe isolation of each of the one or more pulper and/or flashtank units, thereby enabling a reduced operation mode allowing for individual inspection of each pulper and/or flashtank unit under safe conditions, and b) introducing additional bypass routes, e.g. by piping, allowing for the exclusion of each individual pulper and/or flashtank unit from operation. A possible implementation of such additional elements/features and accompanying bypass routes, e.g. by piping, allowing for the continued operation of a plant according to either or examples 1 or 2 above in case of either failures or planned stops of one or more pulper(s) and or flashtank(s) could include:

Piping allowing for the transfer of said liquid substrate, having a dry solids content of between 2 and 30% and a temperature below about 50 C, directly to any of said at least two pulpers (P1(a) and P2(e)), said piping being equipped with one or more closing valve(s) enabling the selection of to which of said at least two pulpers (P1(a) and P2(e)) said liquid substrate, having a dry solids content of between 2 and 30% and a temperature below about 50 C, is to be transferred.

Connections by piping that enables the transfer of said liquid substrate from any of said at least two pulper(s) (P1(a) and P2(e)) to any of said one or more reactors (R (f-i)).

Connections by piping that enables ventilation from any of said one or more reactors (R (f-i)) to any of said at least two pulpers (P1(a) and P2(e))

Connections by piping that enables the transfer of said liquid substrate from any of said one or more reactors (R (f-i)) to any of said one or more flash tank(s)

Connections by piping that enables the by-passing of said, vacuum system (V (c))

When a plant or system according to the present invention is operated in such a reduced operation mode, the plant performance may (for a system or plant with 2 pulpers) be identical to that of a conventional one pulper-one flashtank system.

Another option with such a reduced operation mode is that any single reactor may be excluded from operation, which will keep the plant functional with a reduced capacity. Regardless, the principles of operation remain similar to those described in Examples 1 and 2.

The invention claimed is:

1. A method for thermal hydrolysis of a liquid substrate, having a dry solids content of between 2% and 30% and a temperature below about 50 C, which liquid substrate is subsequently to be used in an anaerobic fermentation, digestion or another process aimed at producing or extracting methane or other valuable substances in one or more reactors, said method being characterized in that: a same number of flashtanks and pulpers are used; at least a first and a second pulper in series and at least a first and a second flashtank in series are used for step-wise pre-heating and pressure reduction, respectively; and in that:

a) said liquid substrate is transferred to and preheated and mixed in a first pulper, which is operated at a temperature of 40 C to 90 C and at a pressure of 0.2 barA to 0.9 barA, by injection of flash steam below liquid level from a downstream flashtank, said second flashtank being operated at a higher pressure than said first pulper;

b) said pressure of 0.2 barA to 0.9 barA, under which said first pulper is being operated, is being maintained by a vacuum system working to maximize condensation of any condensable vapors that are not condensed when passing through said liquid substrate in said first pulper;

c) said preheated liquid substrate is transferred from said first pulper to a second pulper, which is operated at a temperature of 90 C to 135 C and at a pressure of 0.7 barA to 3.3 barA, and wherein said liquid substrate is subjected to further mixing and pre-heating, by injection of flash steam below liquid level from a downstream one of said first and second flashtanks that is operated at a higher pressure than said second pulper;

d) said further preheated liquid substrate is transferred from said second pulper to one or more reactors working in parallel or series wherein said liquid substrate is heated to temperatures in the range of 140 C to 220 C and at a pressure of 3.6 barA to 10 barA;

e) said liquid substrate is transferred from said one or more reactors working in series or parallel to said first flashtank operated at a temperature of 100 C to 140 C and at a pressure of 1 barA to 3.6 barA whereby a pressure reduction occurs, and wherefrom flash steam resulting from said pressure reduction is transferred to said second pulper operated at a temperature of 90 C to 135 C and at a pressure of 0.7 barA to 3.3 barA; and     f) said liquid substrate is transferred from said first flashtank to said second flashtank operated at a temperature of 70 C to 100 C and at a pressure of 0.35 barA to 1 barA, whereby a further pressure reduction occurs, and wherefrom flash steam resulting from said further pressure reduction in said second flashtank is transferred to said first pulper operated at a temperature of 40 C to 90 C and at a pressure of 0.2 barA to 0.9 barA by means of said vacuum system.

2. The method according to claim 1, further characterized in that a vapor cooler, which is interconnected between said first pulper and said vacuum system, works to condense and remove any vapors condensable below the temperature under which said first pulper is being operated.

3. The method according to claim 1, further characterized in that it includes steps aimed at compressing remaining non-condensable vapors from a headspace of said first pulper, which are neither condensed in said first pulper nor in said interconnected vapor cooler and steps aimed at injecting said compressed non-condensable vapors into an anaerobic digester or any other means for gas treatment.

4. The method according to claim 1, wherein the transfer of said liquid substrate between the pulpers, the reactors, and the flashtanks is achieved at least partly by barometrical pumping.

5. A method for thermal hydrolysis of a liquid substrate, having a dry solids content of between 2% and 30% and a temperature below about 50 C, which liquid substrate is subsequently to be used in an anaerobic fermentation, digestion or another process aimed at producing or extracting methane or other valuable substances in one or more reactors, said method being characterized in that: a number of flashtanks used is one less a number of pulpers used; at least a first and a second pulper in series and at least one flashtank are used for step-wise pre-heating and pressure reduction, respectively; and in that:

a) said liquid substrate is transferred to and preheated and mixed in a first pulper, which is operated at a temperature of 40 C to 90 C and at a pressure of 0.2 barA to 0.9 barA, by injection of flash steam below liquid level from a downstream flashtank, which is operated at a higher pressure than said first pulper;

b) said pressure of 0.2 barA to 0.9 barA, under which said first pulper is being operated, is being maintained by a vacuum system working to maximize condensation of any condensable vapors that are not condensed when passing through said liquid substrate in said first pulper;

c) said preheated liquid substrate is transferred from said first pulper to a second pulper, which is operated at a temperature of 90 C to 135 C and at a pressure of 0.7 barA to 3.3 barA, and wherein said liquid substrate is subjected to further mixing and pre-heating, by injection of flash steam below liquid level from one or more downstream reactors, which are operated at a higher pressure than said second pulper;

d) said further preheated liquid substrate is transferred from said second pulper to said one or more reactors working in parallel or series wherein said liquid substrate is heated to temperatures in the range of 140 C to 220 C and at a pressure of 3.6 barA to 10 barA; and     e) said one or more reactors working in parallel or series is depressurized by transferring steam from a reactor headspace to said second pulper until the pressures of said one or more reactors working in parallel or series and said second pulper are in equilibrium following which said liquid substrate is transferred from said one or more reactors working in parallel or series to said downstream flashtank.

6. A plant for thermal hydrolysis of a liquid substrate, having a dry solids content of between 2% and 30% and a temperature of below about 50 C, which liquid substrate is subsequently to be used in an anaerobic fermentation, digestion or another process aimed at producing or extracting methane or other valuable substances, said plant comprising a same number of flashtanks and pulpers, and:

at least a first and a second pulper being interconnected either directly or indirectly in series,     a vacuum system interconnected by piping to one of said at least two pulpers,     one or more reactors working in parallel or series and being interconnected by piping to one of said at least two pulpers, which is not interconnected to said vacuum system,     at least a first and a second flashtank:

being interconnected either directly or indirectly in series,     of which one is interconnected by piping to said one or more reactors working in parallel or series,     of which each is individually interconnected by piping to one of the at least two pulpers, and     of which each is individually capable of being operated at a higher pressure than the one of the at least two pulpers with which it is individually interconnected by piping, and wherein:
a) said first pulper is designed and configured to be operated at a temperature of 40 C to 90 C and at a pressure of 0.2 barA to 0.9 barA, by injection of flash steam below liquid level from one of said at least two downstream flashtanks to which it is individually interconnected,
b) said vacuum system is designed and configured to maintain said pressure of 0.2 barA to 0.9 barA, under which said first pulper is to be operated and to maximize condensation of any condensable vapors that are not condensed when passing through said liquid substrate in said first pulper,
c) said second pulper is designed and configured to be operated at a temperature of 90 C to 135 C and at a pressure of 0.7 barA to 3.3 barA, by injection of flash steam below liquid level from a downstream flashtank to which it is individually interconnected,
d) each of said one or more reactors working in parallel or series is designed and configured to be operated at temperatures in the range of 140 C to 180 C and at a pressure of 3.6 barA to 10 barA,
e) the plant being designed and configured to transfer said liquid substrate from said one or more reactors working in series or parallel to said first flashtank operated at a temperature of 100 C to 140 C and at a pressure of 1 barA to 3.6 barA whereby a pressure reduction occurs, and wherefrom flash steam resulting from said pressure reduction transfers to said second pulper operated at a temperature of 90 C to 135 C and at a pressure of 0.7 barA to 3.3 barA, and
f) the plant being designed and configured to transfer said liquid material from said first flashtank to said second flashtank operated at a temperature of 70 C to 100 C and at a pressure of 0.35 barA to 1 barA, whereby a further pressure reduction occurs, and wherefrom flash steam resulting from said further pressure reduction in said second flashtank transfers to said first pulper operated at a temperature of 40 C to 90 C and at a pressure of 0.2 barA to 0.9 barA by means of said vacuum system.

7. The plant according to claim 6, further comprising a vapor cooler interconnected between said first pulper and said vacuum system, wherein said vapor cooler is designed and configured to be operated at a temperature below the working temperature of said first pulper, thereby enabling removal of condensable vapors that are not condensed in said first pulper.

8. The plant according to claim 6, further characterized in that it includes means for compressing remaining non-condensable vapors from a headspace of said first pulper, which are neither condensed in said first pulper nor in said interconnected vapor cooler and means for injecting said compressed non-condensable vapors into an anaerobic digester or any other means for gas treatment.

9. The plant according to claim 6, further comprising vessels to be used for at least the partial transfer of said liquid substrate by barometrical pumping.

10. The plant according to claim 6, further comprising piping allowing for the transfer of said liquid substrate, having a dry solids content of between 2% and 30% and a temperature below about 50 C, directly to any of said at least two pulpers, said piping being equipped with one or more closing valve(s) enabling selection of to which of said at least two pulpers said liquid substrate, having a dry solids content of between 2% and 30% and a temperature below about 50 C, is to be transferred,
connections by piping that enables the transfer of said liquid substrate from any of said at least two pulper(s) to any of said one or more reactors,
connections by piping that enables ventilation from any of said one or more reactors to any of said at least two pulpers,
connections by piping that enables the transfer of said liquid substrate from any of said one or more reactors to any of said one or more flash tank(s), and
connections by piping that enables the by-passing of said vacuum system.

11. A method for retrofitting an existing plant for hydrolysis of a liquid substrate, having a dry solids content of between 2% and 30% and a temperature below about 50 C, which liquid substrate is to be used in an anaerobic fermentation, digestion or another process aimed at producing or extracting methane or other valuable substances, whereby said retrofitting ensures that said plant comprises at least features of a plant according to claim 6.

12. The method for retrofitting according to claim 11, further comprising ensuring that said plant comprises a vapor cooler interconnected between said first pulper and said vacuum system, wherein said vapor cooler is designed and configured to be operated at a temperature below the operating temperature of said first pulper, thereby enabling removal of condensable vapors that are not condensed in said first pulper.

13. The method for retrofitting according to claim 11, further comprising ensuring that said plant comprises means for compressing remaining non-condensable vapors from a headspace of said first pulper, which are neither condensed in said first pulper nor in said interconnected vapor cooler and means for injecting said compressed non-condensable vapors into an anaerobic digester or any other means for gas treatment.

14. The method for retrofitting according to claim 11, wherein the transfer of said liquid substrate is achieved at least partly by barometrical pumping by a thermal transfer and mixing unit, connected to a live steam system pressurizing a vessel of said unit, and connected to a system to generate a vacuum to increase a filling rate of said vessel of said unit, and wherein said vessel of said unit is equipped to either discharge said liquid substrate to a reactor or return the substrate to a pre-heating vessel.

15. The method for retrofitting according to claim 14, further characterized in that the volume of said thermal transfer and mixing unit is equal to a desired reactor fill volume.

16. The method for retrofitting according to claim 15, further characterized in that said thermal transfer and mixing unit is used to measure reactor filling.

17. The method for retrofitting according to claim 11, further comprising ensuring that said plant comprises:
piping allowing for the transfer of said liquid substrate, having a dry solids content of between 2% and 30% and a temperature below about 50 C, directly to any of said at least two pulpers, said piping being equipped with one or more closing valve(s) enabling selection of to which of said at least two pulpers said liquid substrate, having a dry solids content of between 2% and 30% and a temperature below about 50 C, is to be transferred;
connections by piping that enables the transfer of said liquid substrate from any of said at least two pulpers to any of said one or more reactors;
connections by piping that enables ventilation from any of said one or more reactors to any of said at least two pulpers;

connections by piping that enables the transfer of said liquid substrate from any of said one or more reactors to any of said one or more flash tank(s); and connections by piping that enables the by-passing of said vacuum system.

18. A plant for thermal hydrolysis of a liquid substrate, having a dry solids content of between 2% and 30% and a temperature of below about 50 C, which liquid substrate is to be used in an anaerobic fermentation, digestion or another process aimed at producing or extracting methane or other valuable substances, said plant comprising one more pulper(s) than flashtank(s), and:

at least a first and a second pulper being interconnected either directly or indirectly in series, a vacuum system interconnected by piping to one of said two at least pulpers, one or more reactors working in parallel or series and being interconnected by piping to one of said two at least pulpers, which is not interconnected to said vacuum system, at least one flashtanks:

being interconnected by piping to said one or more reactors working in parallel or series, being interconnected by piping to one of the at least two pulpers, and being capable of being operated at a higher pressure than the one of the at least two pulpers with which it is individually interconnected by piping and wherein:

a) said first pulper is designed and configured to be operated at a temperature of 40 C to 90 C and at a pressure of 0.2 barA to 0.9 barA, by injection of flash steam below liquid level from said downstream flashtank to which it is interconnected;

b) said vacuum system is designed and configured to maintain said pressure of 0.2 barA to 0.9 barA, under which said first pulper is to be operated and to maximize condensation of any condensable vapors that are not condensed when passing through said liquid substrate in said first pulper;

c) said second pulper is designed and configured to be operated at a temperature of 90 C to 135 C and at a pressure of 0.7 barA to 3.3 barA;

d) each of said one or more reactors working in parallel or series is designed and configured to be operated at temperatures in the range of 140 C to 220 C and at a pressure of 3.6 barA to 10 barA; and e) the plant is designed and configured to transfer said liquid substrate from said one or more reactors working in series or parallel to said flashtank, by depressurizing said one or more reactors working in parallel or series by transferring steam from a headspace of the one or more reactors to said second pulper until the pressures of said one or more reactors working in parallel or series and said second pulper are in equilibrium following which said liquid substrate is transferred from said one or more reactors working in parallel or series to said flashtank.

19. A method for retrofitting an existing plant for hydrolysis of a liquid substrate, having a dry solids content of between 2% and 30% and a temperature of below about 50 C, which liquid substrate is to be used in an anaerobic fermentation, digestion or another process aimed at producing or extracting methane or other valuable substances, whereby said retrofitting ensures that said plant comprises at least features of a plant according to claim 18.

* * * * *